United States Patent [19]
Blaisdell et al.

[11] Patent Number: 5,935,098
[45] Date of Patent: Aug. 10, 1999

[54] APPARATUS AND METHOD FOR ACCESSING AND MANIPULATING THE UTERUS

[75] Inventors: Michael W. Blaisdell, Sylvania, Ohio; Piush Vidyarthi, San Francisco; Thomas A. Kramer, San Carlos, both of Calif.

[73] Assignee: Conceptus, Inc., San Carlos, Calif.

[21] Appl. No.: 08/772,707

[22] Filed: Dec. 23, 1996

[51] Int. Cl.⁶ .......................... A61M 31/00; A61M 25/00
[52] U.S. Cl. ............................ 604/55; 604/101; 606/193
[58] Field of Search ................ 606/1, 191, 193, 606/194, 195, 158; 604/55, 174, 96–101, 178

[56] References Cited

U.S. PATENT DOCUMENTS

| | | |
|---|---|---|
| 4,430,076 | 2/1984 | Harris . |
| 4,496,345 | 1/1985 | Hasson . |
| 5,002,557 | 3/1991 | Hasson . |
| 5,104,377 | 4/1992 | LEvine . |
| 5,147,315 | 9/1992 | Weber . |
| 5,176,697 | 1/1993 | Hasson et al. . |
| 5,209,754 | 5/1993 | Ahluwalia . |
| 5,211,627 | 5/1993 | William . |
| 5,259,836 | 11/1993 | Thurmond et al. . |
| 5,273,526 | 12/1993 | Dance et al. . |
| 5,300,023 | 4/1994 | Lowery et al. . |
| 5,372,584 | 12/1994 | Zink et al. . |
| 5,374,247 | 12/1994 | Lowery et al. . |
| 5,389,089 | 2/1995 | Bauer et al. . |

FOREIGN PATENT DOCUMENTS

| | | |
|---|---|---|
| 730355 | 4/1978 | U.S.S.R. . |
| WO 96/22122 | 7/1996 | WIPO . |

OTHER PUBLICATIONS

Product Brochure ZUMI–4.5 , BEI Medical Systems, Inc.

*Primary Examiner*—Michael Buiz
*Assistant Examiner*—William W. Lewis
*Attorney, Agent, or Firm*—Townsend and Townsend and Crew LLP

[57] ABSTRACT

A uterine access catheter system comprises an inner catheter and a sleeve catheter slidably disposed over the inner catheter. The inner catheter is a balloon catheter having an elastomeric balloon near its distal end and suitable for performing hysterosalpingography procedures. The sleeve catheter includes an occluding member near its distal end, and the inner catheter and outer catheter may be used together to seal against and engage the cervix of a patient undergoing hysterosalpingography or other genealogical procedures. The sleeve catheter is locked to the inner catheter, typically relative by relative rotation of the two catheters. The occluding member may be detachable and reusable. Means may be provided for drawing a vacuum between the occluding member and the balloon to further engage the cervical os.

26 Claims, 10 Drawing Sheets

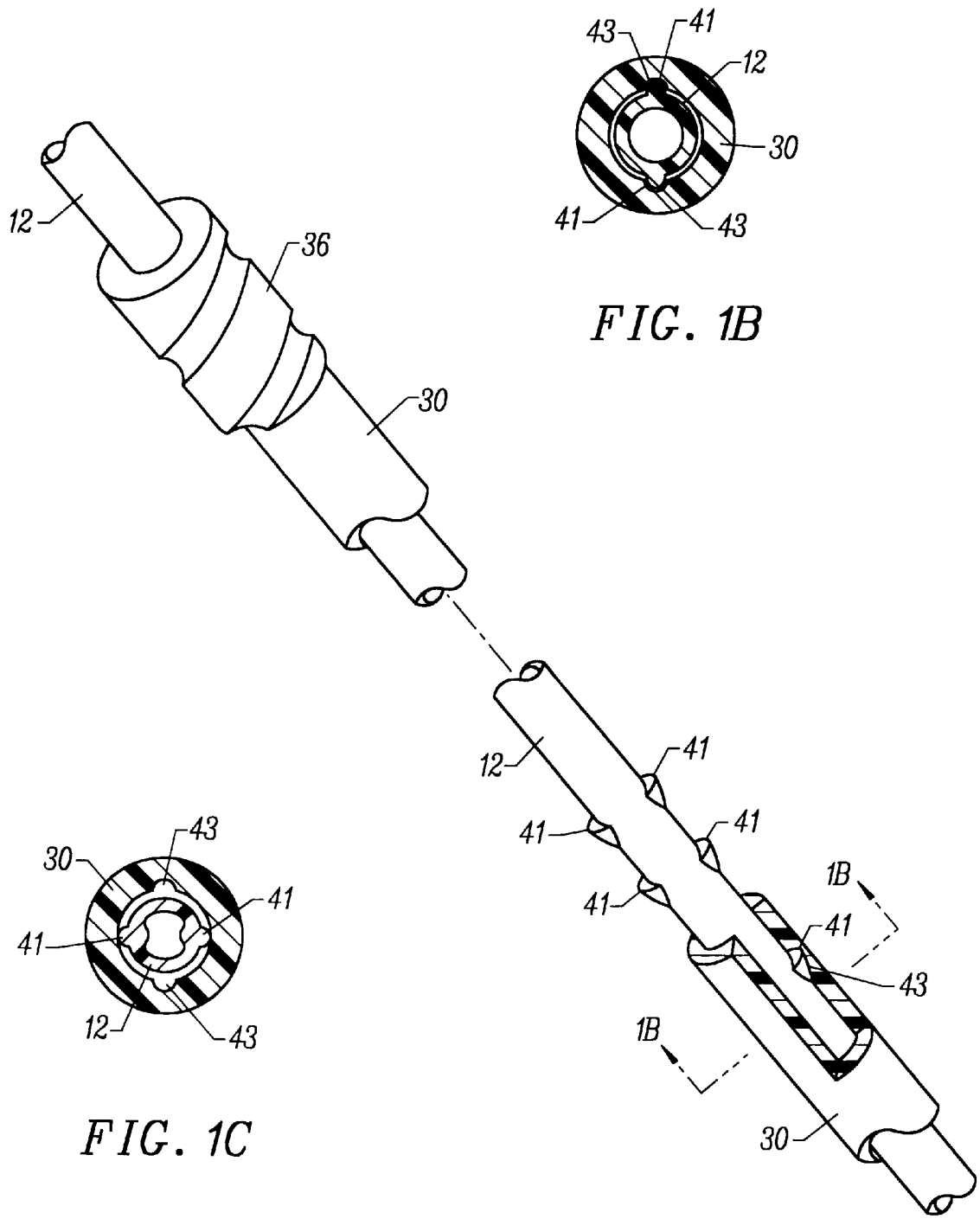

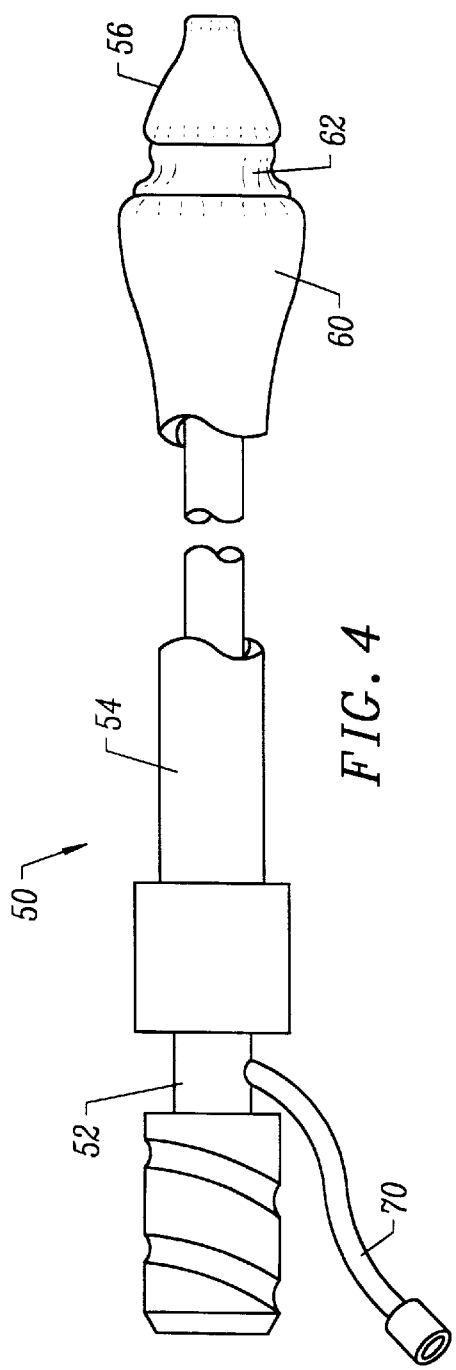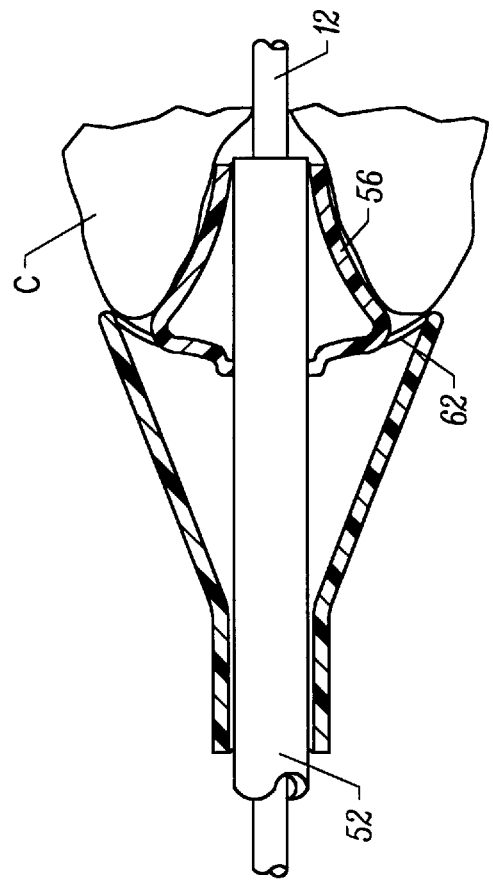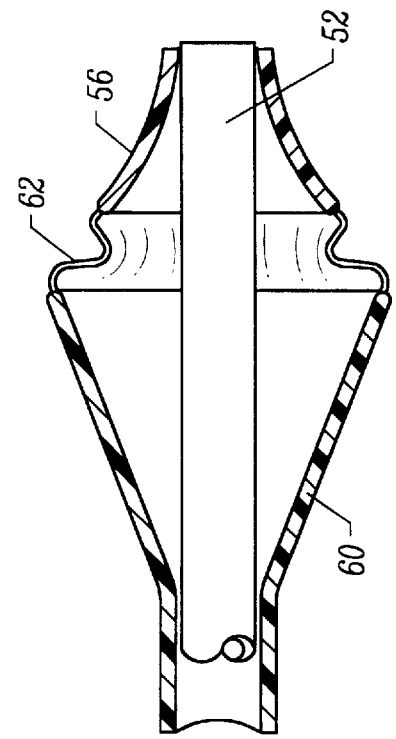
FIG. 4
FIG. 5
FIG. 6

APPARATUS AND METHOD FOR ACCESSING AND MANIPULATING THE UTERUS

The subject matter of the present application is related to copending application Ser. No. 08/772,395 (attorney docket No. 16355-003100), filed on the same day as the present application, the full disclosure of which is incorporated herein by reference.

BACKGROUND OF THE INVENTION

1. Field of the Invention

The present invention relates generally to methods and apparatus for accessing the uterus and optionally the fallopian tubes of a patient. More particularly, the present invention relates to a uterine access catheter system and method which provide for both uterine access and manipulation.

Diseases of the fallopian tubes are a major cause of infertility and tubal pregnancy. Until recently, diagnosis and treatment of tubal disease has been hampered by the difficulty of accessing and imaging the interior of the fallopian tubes in a least invasive manner. Such difficulties, however, have been largely overcome by the present availability of very small guidewires, catheters, and fiberoptic viewing scopes, usually referred to as falloposcopes. Particular systems and methods employing a hysteroscope in combination with the guidewire and small diameter fallopian access catheter for accessing and viewing the interior of the fallopian tubes are described in Kerin et al. (1990) *Fertil. Steril.* 54:390–400 and *J. Laparo. Endoscopic Surg.* 1:47–56, and copending patent application Ser. No. 08/207,475, assigned to the assignee of the present application.

A common medical procedure for imaging the uterus and fallopian tubes is referred to as hysterosalpingography. Such procedures rely on injecting contrast media into the uterus and fallopian tubes using a uterine access catheter having an elastomeric balloon near its distal end for sealing against the cervix. The anatomical structures of the uterus and fallopian tubes are then filled with contrast media fluoroscopically imaged in a conventional manner. In some cases, however, contrast media injected into the uterus does not fully pass into the fallopian tubes. If the fallopian tubes are not filled with the contrast media, subsequent imaging may be inadequate.

In such circumstances, it has been proposed to pass a pair of coaxial catheters through the uterine access catheter in order to access the fallopian tubes. In particular, an outer catheter is used to engage the fallopian os and a smaller tubular catheter is passed through the outer catheter and into the fallopian tube. Contrast media can then be injected directly into the fallopian tube for improved imaging. Such systems are described in U.S. Pat. No. 5,372,584.

While such coaxial catheter systems for selectively accessing the uterus and fallopian tubes are generally successful, they rely on using a relatively large diameter uterine access catheter. In particular, the uterine access catheter must be sufficiently large to pass the coaxial catheter system which is used to enter the fallopian tubes. The need to pass a larger catheter through the cervix significantly increases patient discomfort and can be more difficult for the physician to insert. While it would be possible to initially employ a small catheter for contrast media introduction, subsequent fallopian tube access would then require use of a second, larger uterine access catheter, thus increasing the cost and complexity of the procedure.

A further deficiency of presently utilized uterine access systems is the inability to or difficulty of manipulating the uterus during the hysterosalpingography or other imaging procedure. Frequently, it would be desirable to reorient the uterus to improve the fluoroscopic image or for other purposes. While a variety of uterine manipulating devices exist, most are incapable of fluid injection for fluoroscopic imaging. While combination uterine injectors and manipulators do exist, such as those available from BEI Medical Systems, Inc., under the tradenames ZUMI AND ZUI (which are generally described in U.S. Pat. No. 4,430,076), the handle which is attached over the balloon catheter for engaging the interior surface of the cervical os is difficult to properly position over the inner balloon catheter. Moreover, the handle is useful only for manipulation and does not provide uterine access for the introduction of other uterine and/or fallopian catheters. In contrast, the catheter system described in U.S. Pat. No. 5,372,584, is not useful for uterine manipulation. The '584 catheter has a disk which engages the outside of the cervix to maintain a seal. While sufficient to provide the desired seal, if the '584 catheter were used to manipulate the uterus, the seal provided by the disk would be stressed and the seal lost.

For these reasons, it would be desirable to provide improved apparatus and methods for accessing and manipulating the uterus in hysterosalpingography and other procedures. Such apparatus and methods will preferably provide for the introduction of a small diameter balloon catheter having a sleeve catheter thereover, where the assembly of the balloon catheter and sleeve catheter together provides sufficient rigidity and column strength to permit manipulation of the uterus and wherein the balloon catheter may be withdrawn from the sleeve catheter to permit use of the sleeve catheter for other purposes, such as the introduction of uterine and/or fallopian tube catheters. Such apparatus and methods should reduce the complexity and cost of performing hysterosalpingography and other related uterine and fallopian tube access procedures. It would further desirable if such apparatus were useful for other gynecological procedures, such as treatment of proximal tubal occlusion, endoscopic tubal examination, transcervical gamete intrafallopian transfer (GIFT), therapeutic drug delivery for treatment of infections and ectopic pregnancies, endometrial biopsy, intrauterine ultrasound, and the removal of myomas, polyps, and/or septums, and the like.

2. Description of the Background Art

U.S. Pat. No. 5,372,584, describes a catheter system for performing hysterosalpingography and selective salpingography. Catheter systems and methods for accessing the fallopian tubes are described in U.S. Pat. Nos. 5,389,089; 5,379,247; 5,300,023; and 5,147,315. Catheters intended for uterine access and/or manipulation are described in U.S. Pat. Nos. 5,259,836; 5,104,377, 4,496,345; 4,430,076; and WO 96/22122. Other catheter systems are described in U.S. Pat. Nos. 5,273,526 and 5,211,627. A cervical cannula is described in SU 730355. Laparoscopic cannulas comprising coaxial tubular members are described in U.S. Pat. Nos. 5,002,557 or 5,176,697. A cervical manipulator comprising an inner balloon member and other cervical cap is described in U.S. Pat. No. 5,209,754. Devices manufactured under U.S. Pat. No. 4,430,076, are sold by BEI Medical Systems under the trade name ZUMI, as described in a catalogue of BEI.

A coaxial catheter system for accessing and imaging a fallopian tube is described in copending application Ser. No. 08/207,475, filed on Mar. 7, 1994, assigned to the assignee of the present application, the full disclosure of which is incorporated herein by reference.

SUMMARY OF THE INVENTION

According to the present invention, apparatus and methods are provided for accessing, manipulating, and optionally imaging a patient's uterus and fallopian tubes. The apparatus and methods are particularly suitable for use during the performance of hysterosalpingography where the uterus may be manipulated to improve the image obtained or for other purposes. The apparatus and methods further provide for accessing the fallopian tubes following the hysterosalpingography, but would also find use in a variety of other procedures requiring access to and manipulation of the uterus.

The apparatus and methods are particularly advantageous in that uterine access is provided by a small diameter, usually soft, catheter which is passed through the cervical os into the uterus. Uterine manipulation and subsequent catheter exchange are provided by a second, sleeve catheter which is disposed over the small diameter balloon catheter. The sleeve catheter has an atraumatic occluding member at its distal end which directly engages the interior surface of the cervical os. The occluding member is preferably formed as an inverted cone or "adorn" seal which partially penetrates and seals within the cervix in a manner that permits manipulation without the loss of seal. Together, the inner balloon catheter and sleeve catheter provide sufficient column strength and rigidity so that the uterus can be manipulated from the proximal end of the assembly of the two catheters. The individual catheters, however, are sufficiently small and soft so that the patient suffers minimum discomfort and trauma.

In a first aspect of the present invention, a uterine access catheter system comprises an inner catheter and a sleeve catheter. The inner catheter has a proximal end, a distal end, and a lumen therebetween. An inflatable balloon is positioned near the distal end of the inner catheter. The sleeve catheter has a proximal end, a distal end, and a lumen therebetween, and is sized to slidably receive the inner catheter therethrough. An occluding member is disposed near the distal end of the sleeve catheter and is configured to partially penetrate and seal against an anterior surface of the cervical os when the balloon of the inner catheter is positioned in the uterus. In particular, the sleeve catheter may be advanced distally over the inner catheter to provide for the desired engagement and seal. A locking mechanism is provided on the catheter assembly so that the sleeve catheter may be selectively fixed to the inner catheter to prevent relative axial movement therebetween. In this way, after the inner catheter is introduced and the balloon inflated, the sleeve catheter can be distally advanced to engage the distal occluding member against the anterior surface of the cervical os, providing a good seal and firm mechanical anchor. The sleeve catheter may then be locked to maintain such engagement and seal.

In a particular aspect of the access catheter system, both the inner catheter and the sleeve catheter have dimensions and physical characteristics selected to minimize patient trauma while maintaining sufficient mechanical strength to permit uterine manipulation. In particular, the inner catheter will have an outside diameter in the range from 1 mm to 2.5 mm, preferably from 1.5 mm to 2 mm, a lumen diameter in the range from 0.5 mm to 1.5 mm, usually in the range from 0.5 mm to 0.8 mm, and a length in the range from 25 cm to 40 cm. The sleeve catheter will preferably have an outside diameter in the range from 3 mm to 4.5 mm, usually from 3.3 mm to 4 mm, a lumen diameter in the range from 2 mm to 4 mm, usually from 2.5 mm to 3 mm, and a length in the range from 15 cm to 25 cm, usually from 15 cm to 20 cm. It is particularly preferred that the inner catheter be relatively soft, usually having a hardness in the range from 65D to 75D, preferably from 68D to 74D. The outer catheter will be somewhat harder, usually having a hardness in the range from 65D to 100D, preferably from 70D to 80D. By providing an inner catheter and sleeve catheter having hardnesses within these ranges, the desired mechanical strength is achieved without causing excessive patient discomfort or trauma.

In a specific aspect of the uterine access catheter system of the present invention, the occluding member on the sleeve catheter is formed as a conical plug having its apical end disposed in the distal direction. Optionally, the conical plug or other occluding member may be removably attached to the distal end of the sleeve catheter. Usually, the conical plug or other occluding member will be a resilient structure having a generally fixed geometry (i.e. not inflatable). In alternative embodiments of the present invention, however, the occluding member can be an inflatable balloon, usually having a similar conical configuration when inflated.

In yet another specific aspect of the uterine access catheter system of the present invention, the lock is configured to selectively fix a distal portion of the sleeve catheter to a distal portion of the inner catheter. By locking the inner catheter and sleeve catheter together near their respective distal ends, engagement of the cervix between the balloon and the occluding member may be enhanced. While the present invention contemplates that the catheter lock may be at any axial location within the catheter system, including near the proximal ends, locking mechanisms positioned at or near the proximal end will provide less locking rigidity between the distal ends of the catheters, and is therefore less preferred. Thus, it is preferred that the locking mechanism be dispersed to lock the inner matter to the sleeve catheter in a region within the distal-most 10 cm of the sleeve catheter, more preferably being within the distal-most 5 cm.

In the exemplary embodiment of the catheter lock, a feature is formed on an exterior surface of the inner catheter which selectively engages a mating feature on an inner surface of the sleeve catheter. For example, the feature on the exterior surface of the inner catheter may be a protrusion and the feature on the inner surface of the sleeve catheter may be a recess. After axially aligning the surface features, the catheters can be locked and unlocked to one another to be simply rotating the catheter to move the protrusion(s) and recess(es) in and out of engagement.

In a further specific aspect of the access catheter system in the present invention, the sleeve catheter may further comprise an exterior seal which seals over the interior surface of the cervix when the occluding is in the cervical os. Such a sealing member is particularly useful when the catheter system is provided with a vacuum connector which permits application of a vacuum between the occluding member and the balloon on the inner catheter when the cervix is being engaged therebetween. Application of such a vacuum acts to draw the occluding member into the cervical os, further enhancing engagement and sealing.

In other specific aspects of the uterine access catheter system of the present invention, the inner catheter may further include a hub at its proximal end, and the sleeve catheter may be introduced and removed over the distal end of the inner catheter. Usually, the distal balloon on the inner catheter is elastomeric and can be inflated to a width in the range from 10 mm to 15 mm. The system may further be provided with a stiffening rod that is removably received in the lumen of the inner catheter to facilitate introduction of the inner catheter through the cervical os at the initial stage of a procedure. The stiffening rod may be resilient or may be malleable. Malleable stiffening rods are less traumatic and permit the physician to shape the stiffening rod according to the anatomy of a particular patient. Usually, the sleeve catheter will further include a handle or hub at its proximal end, and more usually the handle will comprise a connective fitting, such as a luer fitting.

In a second aspect of the present invention, methods for accessing the uterus comprise providing a catheter assembly generally as described above. The catheter assembly is introduced through the patient's vagina so that the balloon on the inner catheter is positioned past the cervix and lies within the uterus. The occluding member on the sleeve catheter is then engaged against an interior surface of the cervix, and the balloon inflated to seal against a posterior surface of the cervix. Usually, the balloon will be inflated first to facilitate advancing the occluding member against the cervix. After adequate engagement has been achieved, the sleeve catheter is locked to the inner catheter to prevent relative axial movement.

The catheter assembly introduced and anchored in place as described above is particularly useful for manually manipulating the position of the uterus during hysterosalpingography procedures or for other reasons. Such manual manipulation is achieved by moving the proximal end of the catheter assembly, where the manipulative forces are transmitted through the catheter assembly to the cervix and to within the uterus. The combined column strengths of the inner catheter and the sleeve catheter enhance such force transmission. The preferred dimensions and physical properties of the catheters are set forth above.

In a particularly preferred aspect of the method of the present invention, the locking step comprises rotating the inner catheter relative to the sleeve catheter to selectively engage a surface feature on the inner catheter with a surface feature on the outer catheter. By rotation, it is meant that at least one of the two catheters is rotated about its longitudinal axis relative to the other catheter. Of course, both catheters could be rotated in opposite directions until the desired engagement in locking is achieved. The catheters may then be disengaged by further rotating one catheter relative to the other. The preferred locking mechanisms utilized in the method are described above in connection with system.

Optionally, contrast media is introduced through the inner catheter into the uterus and imaging performed in a hysterosalpingography procedure. After such imaging, the catheters may be unlocked and the inner catheter withdrawn, leaving the sleeve catheter in place. A uterine catheter may then be introduced through the lumen of the sleeve catheter and guided to a fallopian tube falloposcope which can then be guided through the uterine catheter into the fallopian tube and the fallopian tube imaged. Alternatively, contrast media can be introduced through the fallopian tube catheter and the fallopian tube imaged by fluoroscopy. In yet another specific aspect of the method of the present invention, sealing between the occluding member on the sleeve catheter and the anterior surface of the cervical os may be enhanced by drawing a vacuum between the inflated balloon on the inner catheter and the occluding member. Optionally, the ability to draw the vacuum may be enhanced by positioning a seal over the exterior of the cervix before drawing the vacuum.

In still yet another specific aspect of the method of the present invention, the occluding member may be removed from the sleeve catheter after use, sterilized, and reused.

BRIEF DESCRIPTION OF THE DRAWINGS

FIG. 1A is a detailed view with portions broken away of a portion of the sleeve catheter over the inner catheter of the catheter system of FIG. 1, showing a preferred locking mechanism.

FIG. 1B is a cross-sectional view taken along line 1B—1B of FIG. 1A.

FIG. 1C is a cross-sectional view similar to that of FIG. 1B, except that the inner catheter and sleeve catheter have been rotated so that the locking mechanism is out of engagement.

FIGS. 4–6 illustrate a modification to the sleeve catheter of the catheter system of FIG. 1 where an exterior cervical seal and vacuum connection are provided.

DETAILED DESCRIPTION OF THE SPECIFIC EMBODIMENTS

Figure 1:
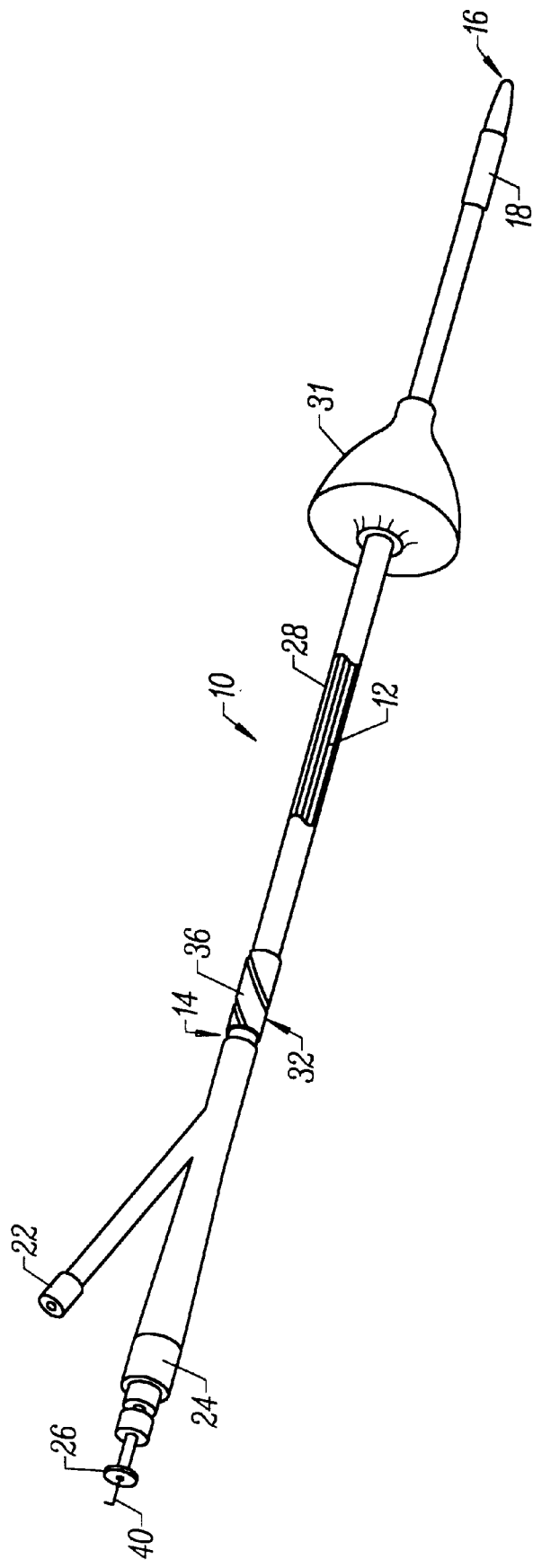
FIG. 1 is a perspective view of a uterine access catheter system constructed in accordance with the principles of the present invention.

A uterine access catheter system according to the present invention is illustrated in FIGS. 1, 1A–1C, and 2. The catheter system 10 comprises two major components, the first of which is an inner catheter 12 having a proximal end 14, a distal end 16, and an inflatable balloon 18 near the distal end. A proximal hub 20 is secured to the proximal end 14 of the inner catheter 12 and includes an inflation port 22 and an axial lumen access port 24. Typically a luer fitting 26 will be located at the proximal end of the proximal hub 20.

The inner catheter 12 preferably comprises a flexible body formed from a soft material, usually a soft thermoplastic polymer or elastomer, such as a polyether block amide (pebax) having a hardness in the range set forth above. The inner catheter 12 will include an axial access lumen 28 and usually a separate inflation lumen (not shown) extending between inflation port 22 and the balloon 18. The access lumen 28 will permit introduction of contrast media to the uterus, as will be described hereinafter. Additional lumens may also be provided, although there will usually be no additional lumens since it is desired to maintain a low profile for the inner catheter to facilitate entry through the cervical os. The preferred dimensions of the inner catheter 12 are set forth above.

The balloon 18 will usually be distensible, more usually being formed from an elastomeric material, optionally being formed from the same material as that used to form the catheter 12 itself. A useful balloon material is polyethylene. The balloon will have dimensions selected to permit inflation within the uterus on the posterior side of the cervical os, usually having a width in the range from 10 mm to 15 mm when fully inflated, more usually being generally spherical.

The second major component of the uterine access catheter system of the present invention is a sleeve catheter 30 which is usually in the form of a simple tube having only a single lumen therethrough and an occluding member 31 positioned at its distal end. Optionally, although not necessarily, a handle which may be in the form of a luer fitting 36 is secured to the proximal end 32 of the sleeve catheter 30.

Figure 2:
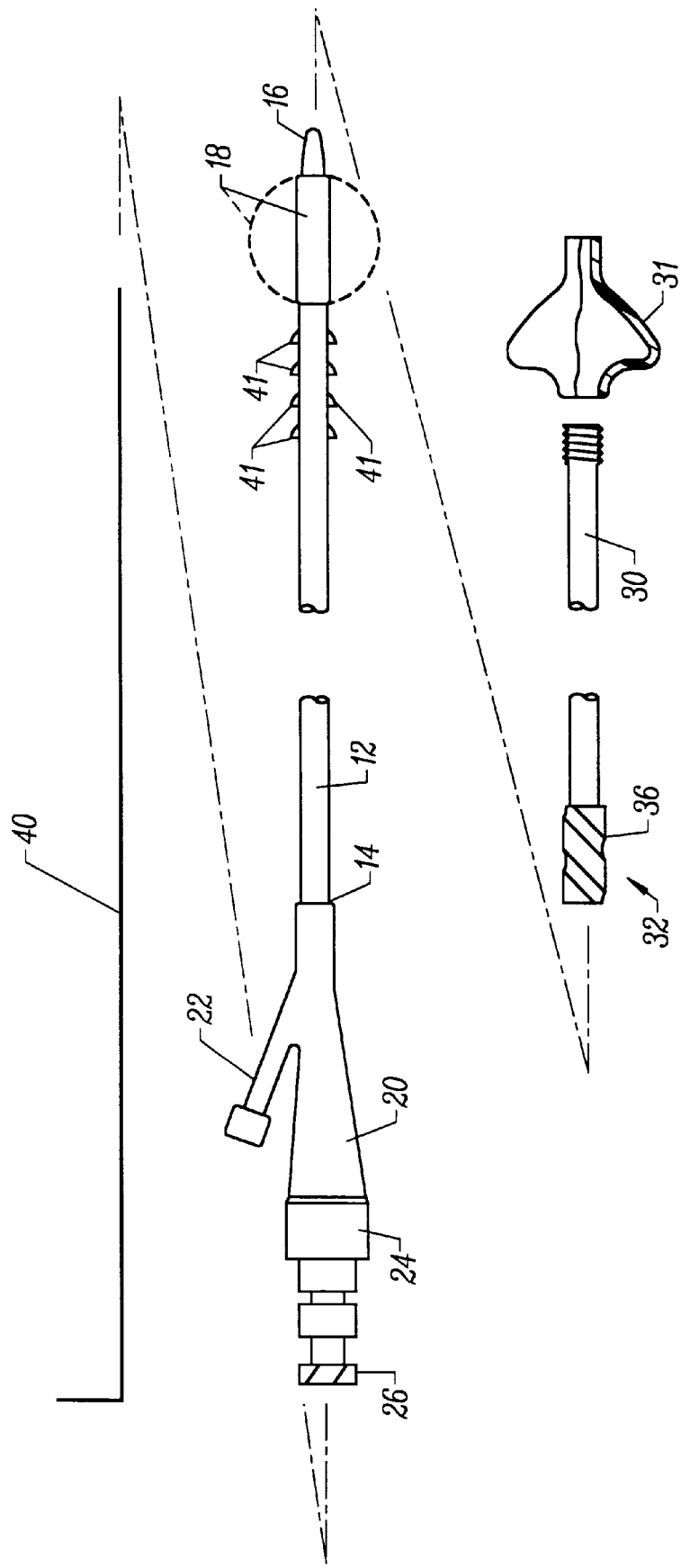
FIG. 2 is an exploded view of the catheter system of FIG. 1.
Figure 2A:
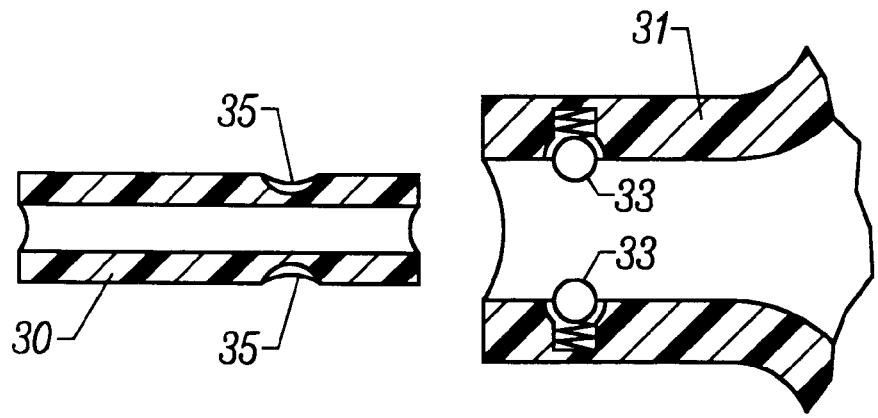
FIG. 2A is a detailed view of an alternative mounting mechanism for a removable occluding member of the sleeve catheter of the catheter system of FIG. 1.
Figure 2B:
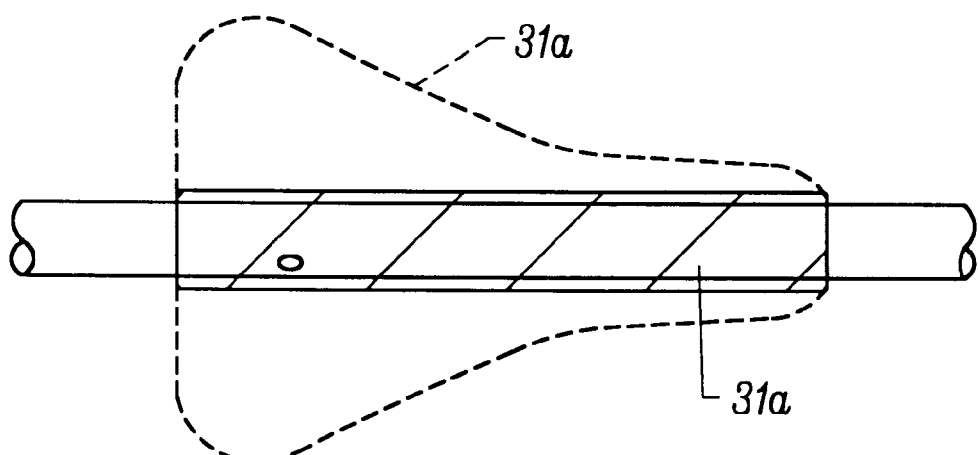
FIG. 2B illustrates an alternative occluding member for the sleeve catheter of the catheter system of FIG. 1, in the form of an inflatable balloon.

The occluding member 31 may be fixedly attached to the distal end of the sleeve catheter 30, but will usually be removably attached thereto. For example, the occluding member 31 may be removably secured to the sleeve catheter 30 by a conventional threaded fitting, as illustrated in FIG. 2, or may be secured to the sleeve catheter by spring-loaded balls 33 in the occluding member 31 and corresponding detents 35 on the distal end of the sleeve catheter 30, as illustrated in FIG. 2A. As yet another alternative, the occluding member 31 can be an inflatable balloon 31a, as illustrated in FIG. 2B, where the inflated configuration is illustrated in broken line. It will be appreciated that the form of the occluding member is not critical so long as it can be selectively engaged against and sealed to the anterior side of the cervical os to permit both manipulation and fluid introduction according to the method of the present invention. Preferably, the geometry will be conical with the apical end disposed distally to partially penetrate and seal against the cervical os.

Referring now in particular to FIGS. 1A–1C, the preferred locking mechanism for the coaxial catheters of the catheter system 10 of the present invention will be described. A plurality of protrusions 41 are formed on the outer surface of inner catheter 12. The protrusions 41 may be in any form, but are preferably formed as small wedges or chevrons which engage similarly shaped recesses 43 formed in the inner surface of the sleeve catheter 30. Preferably, a plurality of protrusions 41 will be axially aligned over one or more lines on the exterior surface of the inner catheter 12. Most preferably, there will be two such lines on opposite sides of the outer surface of the inner catheter 12. In this way, the inner catheter 12 and sleeve catheter 30 can be rotated relative to one another so that the protrusions 41 line up with the recesses 43, as illustrated in FIG. 1B, to lock the catheters together. The catheters can be unlocked simply by rotating the catheters further so that the protrusions 41 fall out of alignment with the recesses 43, as illustrated in FIG. 1C. Usually, more recesses will be provided on the interior surface of the sleeve catheter 30, permitting locking over a range of axial positions. By orienting the wedge-shaped protrusions with the ramped surface declining in the distal direction, as illustrated in FIG. 1A, particular strength is provided to draw proximally on the catheter assembly to manipulate the uterus. Disengagement can be then facilitated by advancing the inner catheter 12 relative to the sleeve.

A stiffening rod or mandrel 40 is optionally provided for inserting through the lumen 28 of the inner catheter 12. The stiffening rod 40 improves the column strength of the inner catheter 12 to facilitate initial introduction through the cervix. After introduction, the stiffening rod 40 can be removed to clear the lumen for introduction of contrast media to perform hysterosalpingography or other procedures. The stiffening rod 40 may be composed of a malleable material, such as stainless steel.

The components of the uterine access catheter system 10 may be packaged separately, but will often be packaged together in a sterile package, such as a pouch, box, or other conventional packaging for medical devices. The uterine access catheter system may be used with other conventional and commercially available catheters for performing fallopian tube access, as described hereinbelow.

Figure 3A:
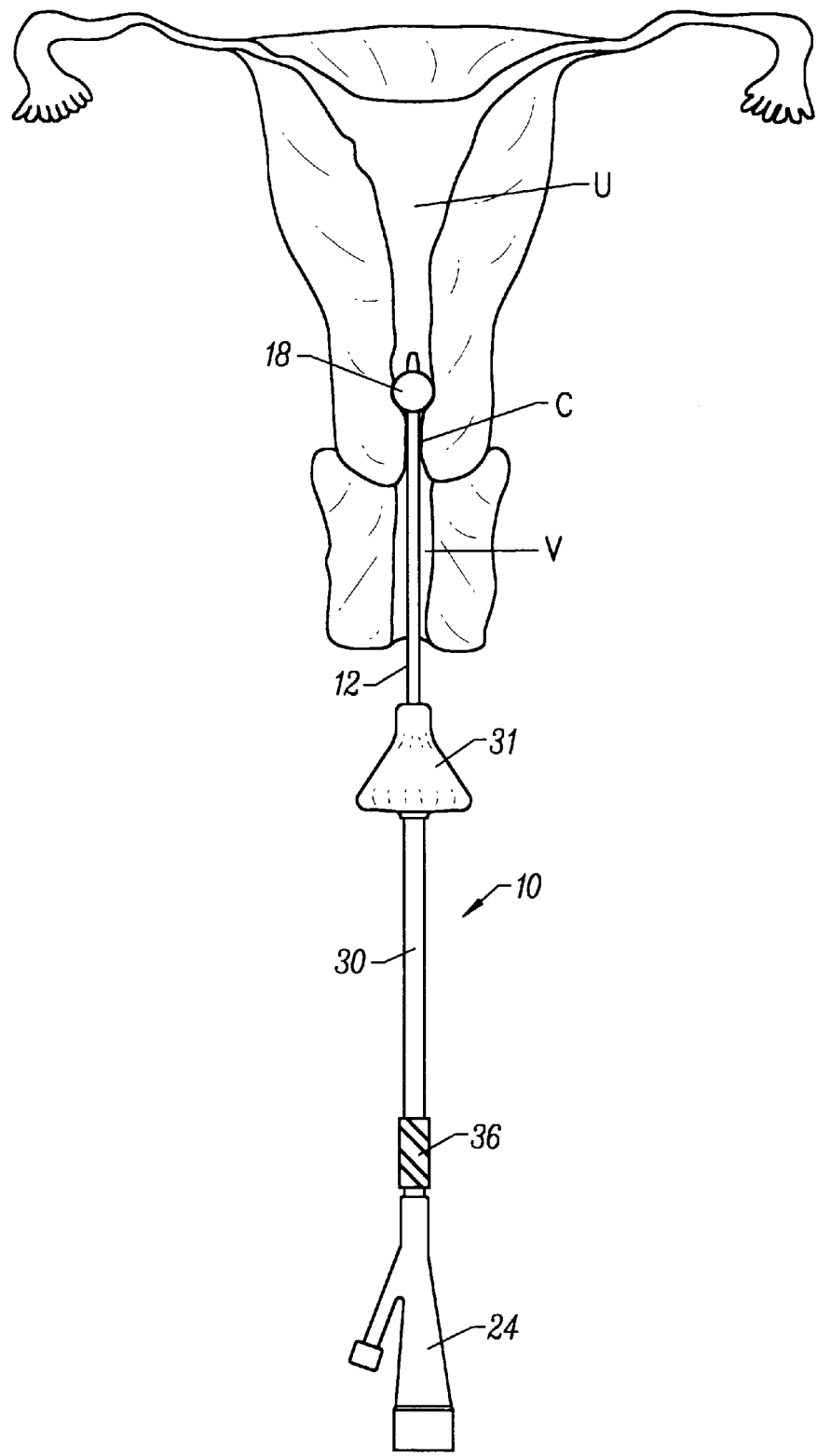
FIGS. 3A–3E illustrate use of the catheter system of FIG. 1 for performing uterine manipulation and a hysterosalpingography procedure followed by accessing the fallopian tube with a fallopian catheter.
Figure 3B:
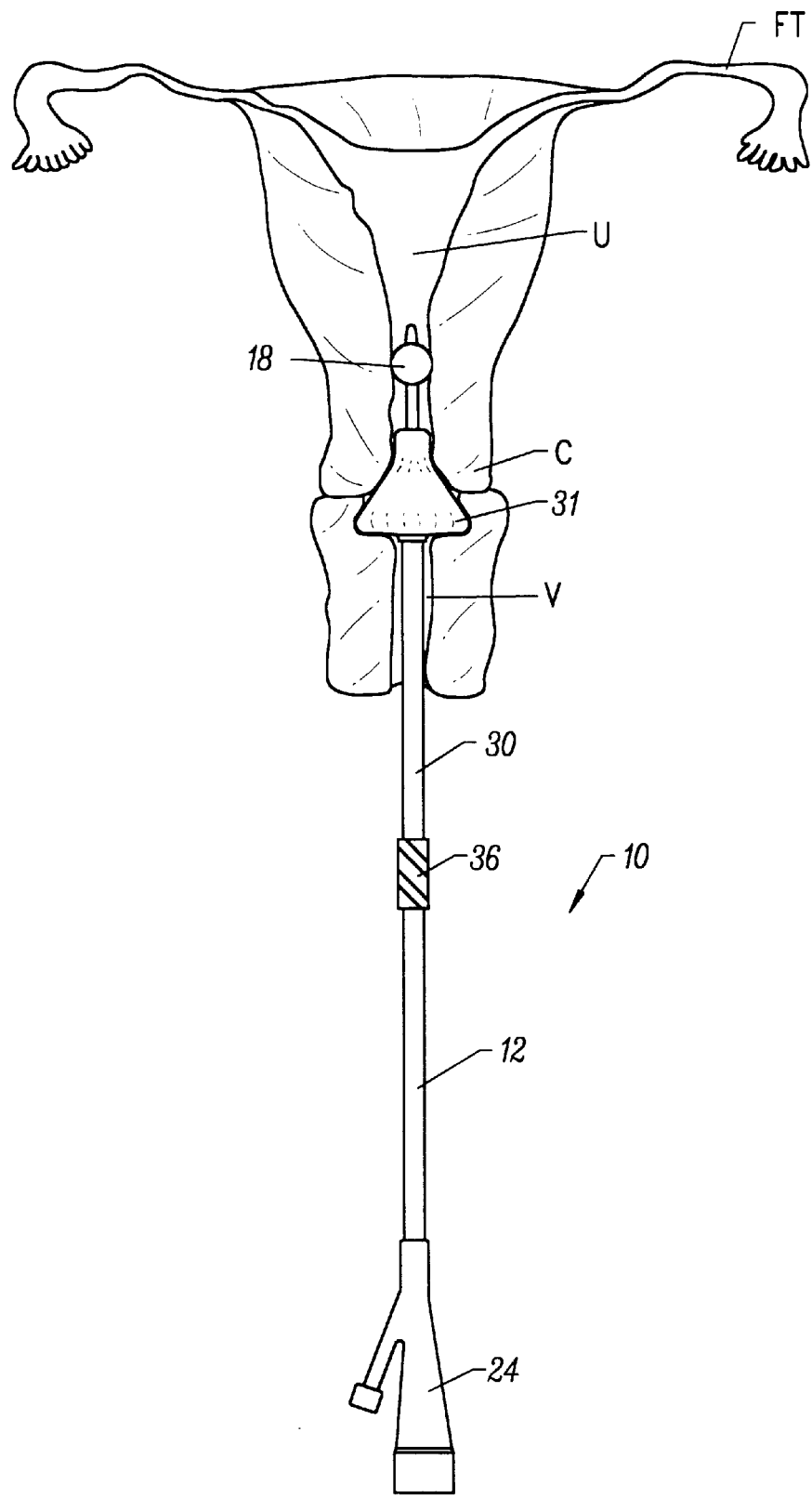

Use of the uterine access catheter system 10 of the present invention for performing hysterosalpingography and manipulating the uterus will now be described in connection with FIGS. 3A–3D. Initially, the access catheter assembly 10 is introduced through the vaginal opening V so that balloon 18 is disposed past cervix C. The balloon is then inflated within the uterus U in order to block outflow from the uterus through the cervix C, as illustrated in FIG. 3A. After appropriately positioning the inner catheter 12, the sleeve catheter 30 is advanced distally over the inner catheter 12 until the occluding member 31 engages an anterior surface of the os of cervix C, as illustrated in FIG. 3B. After the physician feels that the cervical os has been firmly captured between the balloon 18 and the occluding member 31, the sleeve catheter 30 will be locked to the inner catheter 12 by rotating one relative to the other, as described above.

At this point, the catheter assembly is ready either for introduction of contrast media or other fluids through the inner catheter 12 or for manipulation of the uterus using the combined inner catheter 12 and outer sleeve catheter 30. Fluid introduction is achieved through the fluid infusion port 24 on inner catheter 12. Manipulation is achieved by the physician manually grasping a proximal portion of the catheter, typically near the handle 36 of sleeve catheter 30 and moving the assembly until the uterus is positioned in a desired manner.

Figure 3C:
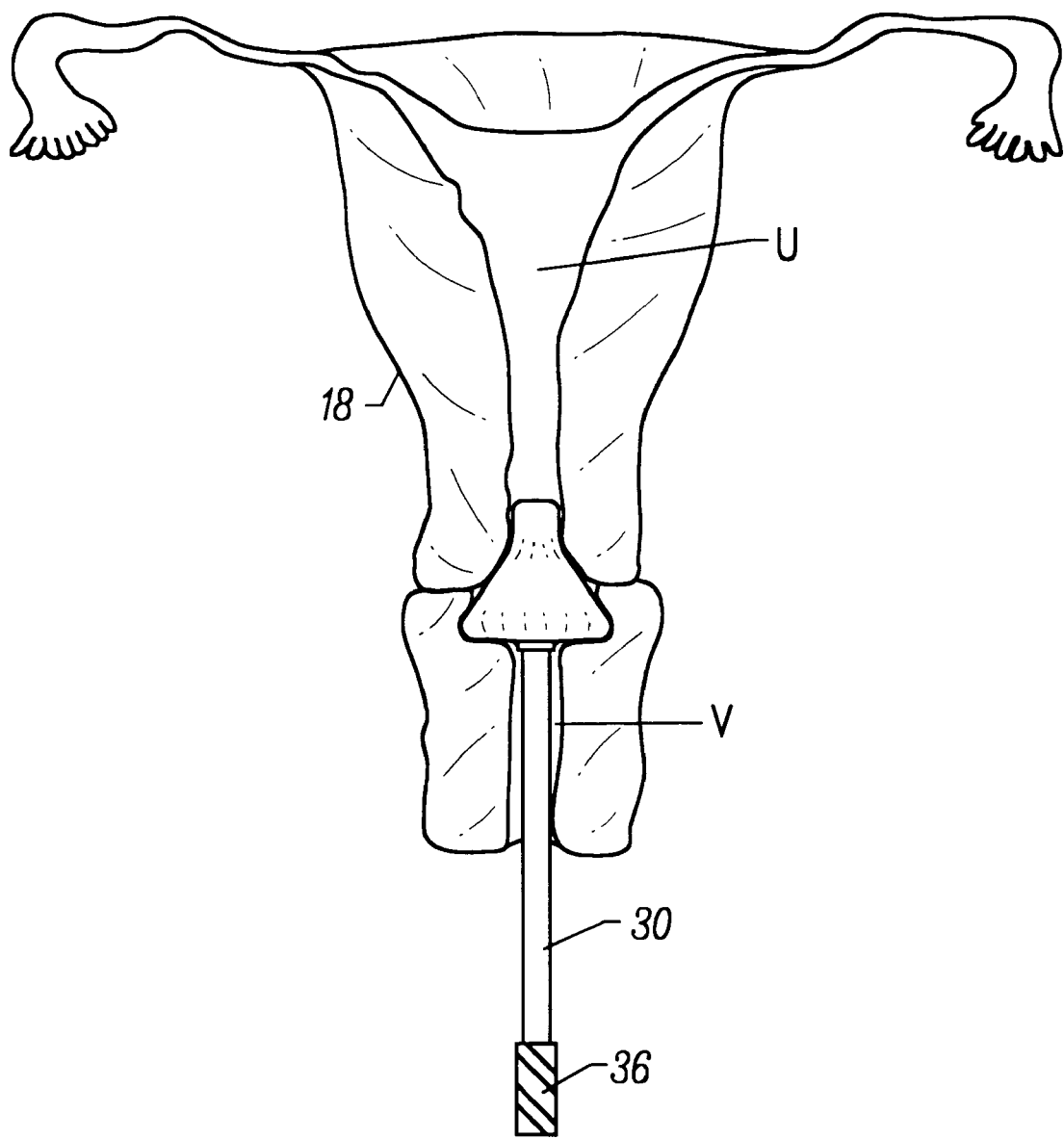
Figure 3D:
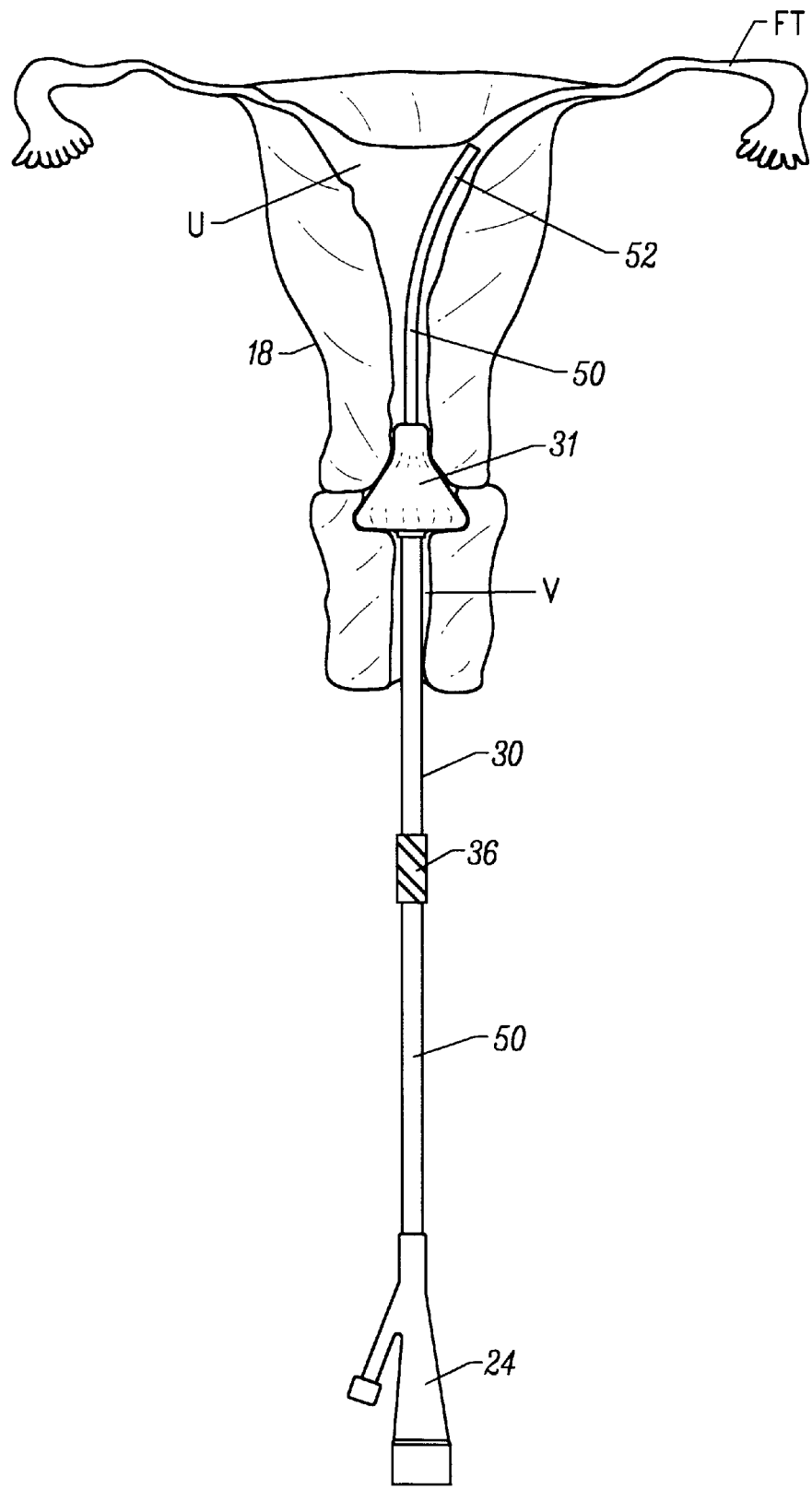

After the initial hysterosalpingography or other procedures completed, the sleeve catheter 30 may be utilized for introduction of other fluid media or other catheters by first removing the inner catheter 12. Such removal is accomplished by rotating the inner catheter relative to the sleeve catheter 30 until they are disengaged. Balloon 18 is deflated, and the inner catheter is withdrawn proximally through the lumen of sleeve catheter 30, resulting in positioning of the sleeve catheter 30 as shown in FIG. 3C. Fluids can be introduced by attaching to the luer fitting 36. Alternatively, a uterine access catheter 50 may be positioned through the lumen of the sleeve catheter 30 into the uterus U, as shown in FIG. 3D. Suitable uterine access catheters are available from commercial suppliers, such as Conceptus, Inc., San Carlos, Calif., under the trade name SOFT TORQUE™. The uterine catheter 50 is positioned so that a deflected end 52 lies adjacent the os of the fallopian tube FT. The uterine catheter 50 thus provides a secondary access lumen directly to the os.

Figure 3E:
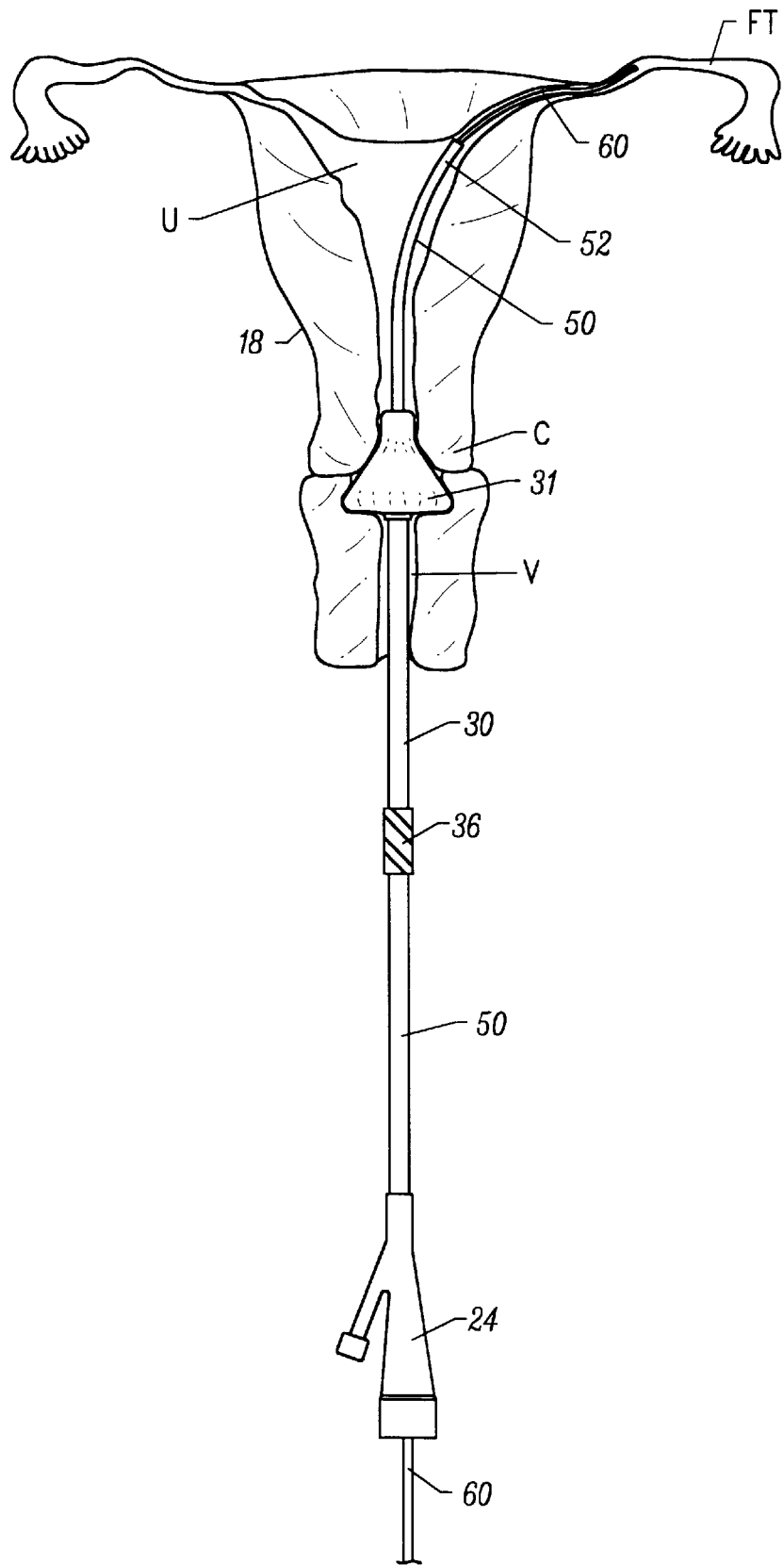

After the uterine catheter 50 has been positioned, a fallopian catheter 60 is passed through the uterine catheter 50, as illustrated in FIG. 3E. Optionally, a guidewire (not illustrated) may be used to position the fallopian catheter 60 within the fallopian tube FT. The fallopian catheter 60 may then be used to provide improved imaging of the fallopian tube. For example, contrast media may be directly injected through the fallopian catheter 60 into the fallopian tube, and fluoroscopic imaging of the tube performed. Alternatively, a falloposcope (not shown) may be introduced through the fallopian catheter 60 and used to image the fallopian tube. Such catheters are commercially available from Conceptus, Inc. under the trade name VS™ catheter. Use of such falloposcopes for imaging a fallopian tube is described in copending application Ser. No. 08/207,475, the full disclosure of which has been previously incorporated herein by reference. The fallopian catheter may be used for other purposes, including treatment of proximal tubal occlusions, and transcervical gamete intrafallopian transfer (GIFT), therapeutic drug delivery for treatment of infectious and ectopic pregnancies, and endometrial biopsy, intrauterine ultrasound, removal of myomas, polyps, and/or septums and the like.

Referring now to FIGS. 4–6, an alternative embodiment of the sleeve catheter of the catheter system of the present invention will be described. Sleeve catheter 50 comprises an inner tubular member 52 and an outer tubular member 54.

The inner tubular member 52 and outer tubular member 54 are arranged coaxially and may be axially translated relative to each other. An occluding member 56 is mounted at the distal end of the inner tubular member 52. A conical cup member 60 is disposed at the distal end of the outer tubular member 54. A flexible seal 62 extends from the distal end of cup 60 to the proximal end of the occluding member 56. By advancing the outer tubular member 54 distally relative to the inner tubular member 52, the flexible seal 62 may be everted, as shown in FIG. 6. In particular, the seal 62 may be everted so that it can engage and seal to the exterior of cervix C to enhance the sealing achieved on the anterior surface of the exterior os. Such sealing may be further enhanced by drawing a vacuum within the cervix C, conveniently by attaching a vacuum source to connector 70 which opens to the annular lumen between the inner luminal surface of inner tubular surface of inner tubular member 52 and the outer surface of inner catheter 12, as shown in FIG. 6. Typically, an "O-ring" or other appropriate seal will be provided distally of the vacuum connector 70 so that a vacuum can be drawn. Drawing a vacuum will further engage both the occluding member 56 and the seal 62 onto the cervix, assuring a fluid tight seal. Such application of a vacuum further enhances the mechanical engagement of the catheter system to the cervix, facilitating manipulation of the uterus as described previously.

Although the foregoing invention has been described in some detail by way of illustration and example, for purposes of clarity of understanding, it will be obvious that certain changes and modifications may be practiced within the scope of the appended claims.

What is claimed is:

1. A method for performing hysterosalpingography on a patient, said method comprising:

providing a catheter assembly including (1) an inner catheter having a balloon near its distal end and (2) a sleeve catheter disposed coaxially over the inner catheter, wherein the sleeve catheter includes an atraumatic occluding member near its distal end;

introducing the catheter assembly through the patient's vagina so that the balloon is positioned past the cervix and in the uterus while the occluding member on the sleeve catheter engages outside the cervix;

inflating the balloon to seal against the cervix;

introducing contrast media through the inner catheter into the uterus;

imaging the uterus; and advancing a distal end of the sleeve catheter over the inner catheter through the cervix and withdrawing the inner catheter from the sleeve catheter to leave an access lumen in the sleeve catheter through the cervix into the uterus.

2. A method as in claim 1, further comprising:

introducing a uterine catheter through the lumen of the sleeve catheter and into the uterus after the sleeve catheter has been advanced into the uterus and the inner catheter removal from the sleeve catheter; and guiding a distal end of the uterine catheter to the os at the entrance to a fallopian tube.

3. A method as in claim 2, further comprising:
   passing a fallopian catheter through a lumen of the uterine catheter and into the fallopian tube.

4. A method as in claim 3, further comprising:
   passing a falloposcope through a lumen of the fallopian catheter; and imaging the fallopian tube using the falloposcope.

5. A method as in claim 3, further comprising
   introducing contrast media through the fallopian catheter into the fallopian tube; and
   imaging the fallopian tube.

6. A method as in claim 1, further comprising infusing of aspirating a fluid or material through the sleeve catheter into the uterus after the sleeve catheter has been advanced into the uterus and the inner catheter removed from the lumen of the sleeve catheter.

7. A method as in claim 1, wherein the catheter system further comprises a stiffening rod that is removably received in a lumen of the inner catheter, wherein the stiffening rod is in place when the catheter system is introduced through the vagina and cervix and is removed prior to introducing contact media into the uterus.

8. A method as in claim 7, wherein the stiffening rod is malleable and further comprising shaping a portion of the stiffening rod so that the inner catheter assumes a shape selected to match the patient's anatomy.

9. A uterine access catheter system comprising:

an inner catheter having a proximal end, a distal end, an access lumen therebetween, and an inflatable balloon near the distal end;

a sleeve catheter having a proximal end, a distal end, and a lumen therebetween sized to slidably receive the inner catheter, wherein the length of the sleeve catheter is less than the length of the inner catheter by at least 5 cm so that the distal end of the inner catheter can be introduced through a patient's cervix while the distal end of the sleeve catheter remains outside of the cervix; and an occluding member on the distal end of the sleeve catheter adapted to engage against the outside of a cervical os when the inner catheter passes through the cervix and the sleeve catheter is placed over the inner catheter.

10. A uterine access catheter system as in claim 9, wherein the inner catheter further includes a hub at its proximal end, wherein the sleeve catheter may be introduced and removed over the distal end of the inner catheter.

11. A uterine access catheter system as in claim 10, wherein the inner catheter has an outside diameter in the range from 1 mm to 2.5 mm and a lumen diameter in the range from 0.5 mm to 1.5 mm, a length from 25 cm to 40 cm, and wherein the sleeve catheter has a lumen diameter in the range from 2 mm to 4 mm, an outside diameter in the range from 3 mm to 4.5 mm, and a length in the range from 15 cm to 25 cm.

12. A uterine access catheter system, as in claim 11, wherein the distal balloon is elastomeric and can be inflated to a width in the range from 10 mm to 15 mm.

13. A uterine access catheter system, as in claim 9, wherein the inner catheter is composed of a soft material having a hardness in the range from 65D to 75D, and the sleeve catheter is composed of a material having a hardness in the range from 70D to 80D.

14. A uterine access catheter system as in claim 9, wherein the stiffening rod is malleable over at least a distal portion thereof.

15. A uterine access catheter system as in claim 9, wherein the stiffening rod is resilient.

16. A uterine access catheter system as in claim 9, wherein the sleeve catheter is more rigid than the inner catheter.

17. A uterine access catheter system as in claim 9, wherein the sleeve catheter comprises a handle at its proximal end.

18. A uterine access catheter system as in claim 17, wherein the handle comprises a connectable fitting.

19. A method for performing hysterosalpingography on a patient, said method comprising:

provide a catheter assembly including (1) an inner catheter having a balloon near its distal end and (2) a sleeve catheter disposed coaxially over the inner catheter, wherein the sleeve catheter includes an atraumatic occluding member near its distal end;

introducing the catheter assembly through the patient's vagina so that the balloon is positioned past the cervix and in the uterus while the occluding member on the sleeve catheter engages outside the cervix;

inflating the balloon to seal against the cervix;

introducing contrast media through the inner catheter into the uterus;

imaging the uterus;

introducing a uterine catheter through the lumen of the sleeve catheter and into the uterus after the sleeve catheter has been advanced into the uterus and the inner catheter removal from the sleeve catheter; and guiding a distal end of the uterine catheter to the os at the entrance to a fallopian tube passing a falloposcope through a lumen of the fallopian catheter; and imaging the fallopian tube using the falloposcope.

20. A method as in claim 19, further comprising
introducing contrast media through the fallopian catheter into the fallopian tube; and
imaging the fallopian tube.

21. A method as in claim 19, further comprising advancing the sleeve catheter into the uterus; removing the inner catheter from the lumen of the sleeve catheter; and infusing of aspirating a fluid or material through the sleeve catheter into the uterus.

22. A method as in claim 19, wherein the catheter system further comprises a stiffening rod that is removably received in a lumen of the inner catheter, wherein the stiffening rod is in place when the catheter system is introduced through the vagina and cervix and is removed prior to introducing contact media into the uterus.

23. A method as in claim 22, wherein the stiffening rod is malleable and further comprising shaping a portion of the stiffening rod so that the inner catheter assumes a shape selected to match the patient's anatomy.

24. A method for performing hysterosalpingography on a patient, said method comprising:

providing a catheter assembly including (1) an inner catheter having a balloon near its distal end, (2) a sleeve catheter disposed coaxially over the inner catheter, wherein the sleeve catheter includes an atraumatic occluding member near its distal end, and (3) a stiffening rod that is removably received in a lumen of the inner catheter;

introducing the catheter assembly through the patient's vagina with the stiffening rod in place in the inner catheter lumen so that the balloon is positioned past the cervix and in the uterus while the occluding member on the sleeve catheter engages outside the cervix;

inflating the balloon to seal against the cervix;

removing the stiffening rod; and introducing contrast media through the inner catheter into the uterus;

imaging the uterus.

25. A method as in claim 24, further comprising:

introducing a uterine catheter through the lumen of the sleeve catheter and into the uterus after the sleeve catheter has been advanced into the uterus and the inner catheter removal from the sleeve catheter; and guiding a distal end of the uterine catheter to the os at the entrance to a fallopian tube.

26. A method as in claim 24, further comprising:

passing a falloposcope through a lumen of the fallopian catheter; and imaging the fallopian tube using the falloposcope.

* * * * *